US008967143B2

(12) United States Patent
Gutmark et al.

(10) Patent No.: US 8,967,143 B2
(45) Date of Patent: Mar. 3, 2015

(54) ACOUSTIC PRESSURE INDUCERS AND METHODS FOR TREATMENT OF OBSTRUCTIVE SLEEP APNEA

(75) Inventors: Ephraim Gutmark, Cincinnati, OH (US); Siddarth Khosia, Cincinnati, OH (US); Liran Oren, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 410 days.

(21) Appl. No.: 13/561,762

(22) Filed: Jul. 30, 2012

(65) Prior Publication Data

US 2013/0186399 A1   Jul. 25, 2013

Related U.S. Application Data

(60) Provisional application No. 61/513,253, filed on Jul. 29, 2011.

(51) Int. Cl.

| A61M 11/00 | (2006.01) |
| A61M 16/00 | (2006.01) |
| F04B 43/04 | (2006.01) |
| A61M 16/06 | (2006.01) |
| A61M 16/08 | (2006.01) |

(52) U.S. Cl.
CPC .......... *A61M 16/0057* (2013.01); *F04B 43/046* (2013.01); *A61M 16/0666* (2013.01); *A61M 2205/8206* (2013.01); *A61M 16/0875* (2013.01); *A61M 2206/16* (2013.01)
USPC ............. 128/204.18; 128/206.21; 128/207.18

(58) Field of Classification Search
USPC ............. 128/204.18–204.23, 206.21, 207.13, 128/207.18
See application file for complete search history.

(56) References Cited

U.S. PATENT DOCUMENTS

| 2,918,917 A | 12/1959 | Emerson |
| 4,602,644 A * | 7/1986 | DiBenedetto et al. ......... 600/538 |
| 5,307,794 A * | 5/1994 | Rauterkus et al. ....... 128/204.18 |

(Continued)

FOREIGN PATENT DOCUMENTS

| EP | 1655052 A2 | 5/2006 |
| GB | 2177311 A | 1/1987 |
| WO | 98/47463 A1 | 10/1998 |

OTHER PUBLICATIONS

International Application No. PCT/US12/48828 Filed Jul. 30, 2012, International Search Report and Written Opinion, mailed Nov. 6, 2012.

*Primary Examiner* — Steven Douglas
(74) *Attorney, Agent, or Firm* — Denise M. Everett (57) ABSTRACT

Acoustic pressure inducers and methods for treating obstructive sleep apnea are disclosed. In one embodiment, an acoustic pressure inducer includes an actuator housing having an orifice, a tube having a first end and a second end, and a nasal cannula fluidly coupled to the second end of the tube. The first end of the tube is fluidly coupled to the orifice of the actuator housing such that a gap is present between the first end of the tube and the orifice. The nasal cannula is configured to be positioned proximate to nostrils of a user. The acoustic pressure inducer further includes a vibrating element within the actuator housing and a signal generator. The signal generator component is electrically coupled to the vibrating element and configured to provide an electronic signal to the vibrating element to cause the vibrating element to oscillate within the actuator housing and produce an acoustic jet of air that exits the orifice and enters a nasal passageway of the user through the nasal cannula.

20 Claims, 12 Drawing Sheets

(56) References Cited

U.S. PATENT DOCUMENTS

| | | | |
|---|---|---|---|
| 5,611,335 A * | 3/1997 | Makhoul et al. | 128/204.24 |
| 5,893,361 A * | 4/1999 | Hughes | 128/200.24 |
| 6,152,130 A * | 11/2000 | Abrams et al. | 128/204.21 |
| 6,457,654 B1 | 10/2002 | Glezer et al. | |
| 8,539,952 B2 * | 9/2013 | Carbone et al. | 128/205.24 |
| 8,702,379 B2 * | 4/2014 | Frater et al. | 415/119 |
| 2009/0098015 A1 | 4/2009 | Bhardwaj | |

* cited by examiner

FIG. 13

ACOUSTIC PRESSURE INDUCERS AND METHODS FOR TREATMENT OF OBSTRUCTIVE SLEEP APNEA

CROSS-REFERENCE TO RELATED APPLICATIONS

This application claims the benefit of U.S. Provisional Patent Application Ser. No. 61/513,253, filed on Jul. 29, 2011, the entire disclosure of which is hereby incorporated herein by reference.

BACKGROUND

Approximately 15 million Americans have obstructive sleep apnea (OSA). Portions of the respiratory tract collapse in OSA patients resulting in the blockage of the airways and reduced blood oxygen levels. As blood oxygen levels drop, the patient awakens and gasps for air. This cycle is repeated many times during the night. Left untreated, OSA is associated with a significant increased risk of cardiovascular events including hypertension, stroke and heart attack. Obstructive sleep apnea has been associated with a high risk for motor vehicle accidents, and is thought to account for 15-20% of the 40-50,000 deaths and almost 4,000,000 emergency department visits annually. Continuous Positive Air Pressure, or CPAP, is an effective and widely recognized therapy for obstructive sleep apnea but is often under prescribed by physicians and under-utilized by patients. The positive air pressure prevents the airways of the respiratory tract from collapsing, preventing the apneic event.

The basic mechanism of a CPAP device is based on creating a positive pressure gradient between the device and the patient. As a result, when the mask is open to atmosphere, a constant jet will be generated from the pressure gradient between the device and the atmosphere. When the mask is placed around the patient's face, the jet is stopped and a positive pressure builds between the CPAP and the lungs of the patient. This positive pressure maintains the airways from collapsing. If the mask is not sealed correctly, the air will then follow the path of least resistance, thus escaping out into the atmosphere where the pressure is lower. The patient will experience this as air bleeding out from the system, but more importantly, the positive pressure that is the basic of operation for CPAP cannot be maintained. A tight fluid seal is required to maintain a positive air pressure throughout the entire upper airway. If the fluid seal is broken, continuous positive pressure is lost and the patient's upper airways are at risk of collapsing. To prevent this pressure loss, a tight seal in the form of a mask must be placed over the mouth and nose.

An alternative to a full face mask is a nasal apparatus that only works if the patient does not open his or her mouth at night. If the patient opens his or her mouth, the fully pressurized respiratory tract will lose pressurization as the air will follow the path of least resistance and rush out of the mouth. For patients that open their mouths, an additional apparatus to keep the mouth closed must be employed. Chin straps and bite guards are two approaches to help mouth breathers keep their mouths closed during sleep.

CPAP is efficacious, but is not well tolerated by patients. Studies show that somewhere between 46% and 83% of patients are not compliant with CPAP therapy and remove the CPAP device early in the night or skip use altogether. Compliance is poor due to the discomfort and inconvenience associated with CPAP. Issues that result in patient non-compliance include mask discomfort, nasal dryness, congestion, difficulty adapting to the unrelenting positive air pressure across the mouth and nose, abdominal bloating due to air entering the digestive tract, and facial skin irritation due to the requirement of a tight seal between the mask and face.

Accordingly, a need exists for alternative treatments for obstructive sleep apnea.

SUMMARY

In one embodiment, an acoustic pressure inducer for treatment of obstructive sleep apnea includes an actuator housing having an orifice, a tube having a first end and a second end, and a nasal cannula fluidly coupled to the second end of the tube. The first end of the tube is fluidly coupled to the orifice of the actuator housing such that a gap is present between the first end of the tube and the orifice. The nasal cannula is configured to be positioned proximate to the nostrils of a user. The acoustic pressure inducer further includes a vibrating element within the actuator housing and a signal generator. The vibrating element and the actuator housing define an acoustic chamber that is fluidly coupled to the orifice. The signal generator component is electrically coupled to the vibrating element and configured to provide an electronic signal to the vibrating element to cause the vibrating element to oscillate within the actuator housing. Oscillation of the vibrating element produces an acoustic jet of air defined by a train of vortices. The acoustic jet of air exits the orifice and enters a nasal passageway of the user through the nasal cannula generating positive pressure to prevent respiratory tract occlusion.

In another embodiment, a method of treating obstructive sleep apnea includes generating an acoustic jet of air defined by a train of vortices produced by oscillatory motion of a vibrating element within an actuator housing such that the acoustic jet of air exits an acoustic chamber defined by the vibrating element and the actuator housing through an orifice. The method further includes directing the acoustic jet of air into a nasal passageway of a user through a nasal cannula.

In yet another embodiment, an acoustic pressure inducer for treatment of obstructive sleep apnea includes an actuator housing having an orifice, a tube having a first end fluidly coupled to the orifice of the actuator housing, and a vibrating element within the actuator housing. A gap is present between the first end of the tube and the orifice. The vibrating element and the actuator housing define an acoustic chamber that is fluidly coupled to the orifice. The acoustic pressure inducer further includes a signal generator component electrically coupled to the vibrating element and configured to provide an electronic signal to the vibrating element to cause the vibrating element to oscillate within the actuator housing. Oscillation of the vibrating element produces an acoustic jet of air defined by a train of vortices. The acoustic jet of air exits the orifice and enters a nasal passageway of a user through the second end of the tube without a fluid seal at the nostrils of the user to prevent respiratory tract occlusion.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Embodiments of the present disclosure are directed to devices and methods for the treatment of obstructive sleep apnea that utilize an acoustic pressure inducer to solve many of the problematic issues associated with CPAP therapy without compromising therapy effectiveness.

Generally, embodiments of the present disclosure produce an extremely coherent acoustic jet of air, a quality that makes its initial trajectory independent of the conditions around it (i.e. if the mask is sealed or not). The laws of physics demonstrate that a pressurized airstream (gas) flows from an area of high pressure to an area of lower pressure. In the case of CPAP, the airstream takes the path of least resistance, such as out the side of an ill-fitting mask or out of a patient's mouth. However, embodiments of the present disclosure produce a train of vortices with mass flow that is sufficient to produce enough pressure to keep the airways of the respiratory tract from collapsing. The acoustic jets of air of the devices described below create pressurized air streams that flow in a manner that disregards the observation that a pressurized gas or airstream will take the path of least resistance because of the match between the impedance of the acoustic jet and the impedance of the nasal tract. The acoustic jet needs only to be directed towards the nostrils of the patient to give a desired effect of preventing respiratory occlusion. A nasal cannula off-set from the nostril will deliver a stream of air that selectively enters the nose and then subsequently selectively enters the respiratory tract without a loss of pressurized airflow from the mouth. Accordingly, embodiments of the present disclosure may circumvent the need to provide the tight seals required of traditional CPAP devices because they do not rely on pressurizing the entire respiratory tract.

Various embodiments of acoustic pressure inducers and methods for treating obstructive sleep apnea using acoustic jets of air are described in detail below.

Figure 1:
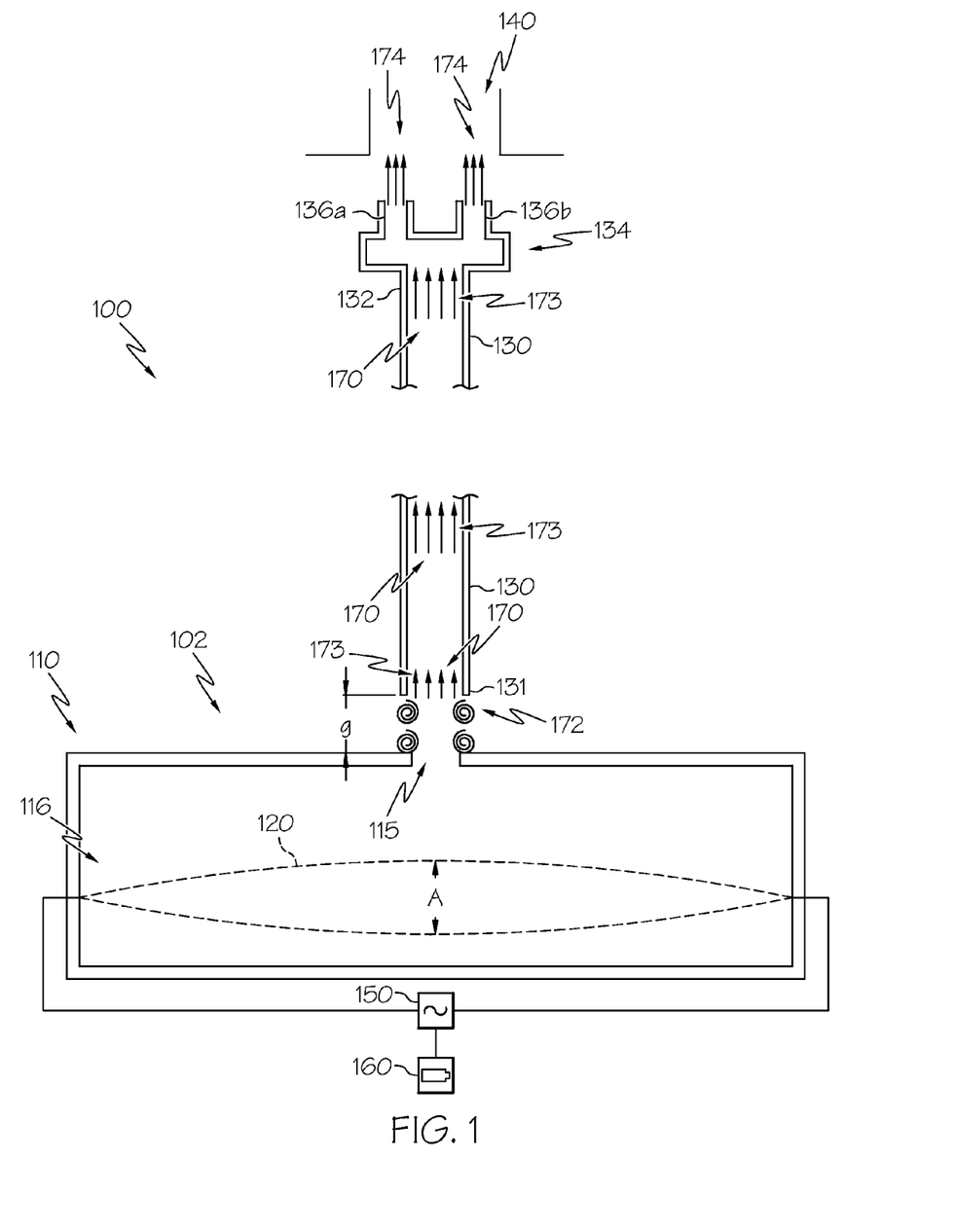
FIG. 1 schematically depicts an exemplary acoustic pressure inducer fluidly coupled to a respiratory tract of a user according to one or more embodiments described and illustrated herein.

Referring now to FIG. 1, an exemplary acoustic pressure inducer 100 for treatment of obstructive sleep apnea is schematically depicted. The acoustic pressure inducer 100 generally includes an actuator 102 comprising a vibrating element 120 disposed within an actuator housing 110. The vibrating element 120 and the actuator housing 110 define an acoustic chamber 116. The actuator housing 110 further includes an orifice 115 (or nozzle) that is fluidly coupled to the acoustic chamber 116.

The vibrating element 120 is configured as a vibrating member that, when excited, oscillates back and forth as indicated by arrow A, and produces an acoustic jet of air 170 that exits the orifice 115. The acoustic pressure inducer 100 further includes a signal generator component 150 electrically coupled to a power supply 160. In some embodiments, the signal generator component 150 and the power supply 160 are a single component. In other embodiments, the signal generator component 150 and the power supply 160 are separate components. Because of the low energy requirements of the acoustic pressure inducer 100 to achieve airflows sufficient for efficacy, the power supply 160 may be configured as a battery power source. However, electrical power may also be provided by connection to an external power supply, such as an electrical grid system or generator. The signal generator component 150 is configured to provide one or more electrical signals to the vibrating element 120 to cause it to oscillate back and forth. The type of electrical signal may depend on the type of vibrating element.

The vibrating element 120 may be configured as any actuator capable of oscillating a diaphragm or other similar member to produce the acoustic jet of air 170. In one embodiment, the vibrating element is configured as a piezoelectric diaphragm that oscillates back and forth in response to an alternating current (AC) signal, such as a sine wave or a square wave, for example. The piezoelectric vibrating element 120 may be a flexible membrane with a thickness approximating a piece of heavy weight paper, for example. The signal generator component 150, which may be configured as a function generator and an amplifier, is operable to provide an electrical signal to the vibrating element 120 at the desired frequency.

The vibrating element 120 may be configured as an actuator device other than a piezoelectric actuator. For example, the vibrating element 120 may be an electric motor, a shape memory allow actuator, a magnetic actuator (e.g., a speaker device), a plasma actuator, a piston, and the like. In other embodiments, multiple vibrating elements 120 may be provided in the acoustic chamber 116. Further, multiple orifices 115 may be provided to produce single or multiple outputs. For example, the actuator 102 may be configured as cubical in shape, with one or more orifices on one or more sides and one or more vibrating elements on one or more sides.

The exemplary acoustic pressure inducer 100 further includes a tube 130 having a first end 131 that is fluidly coupled to the orifice 115 of the actuator housing 110 and a second end 132 that is fluidly coupled to a nasal cannula 134. The nasal cannula 134 includes two prongs 136a and 136b that are configured to be positioned proximate to the nostrils of a user. As described in more detail below, the acoustic jet of air 170 exits the orifice 115 of the actuator housing 110, travels through the tube 130, exits the nasal cannula 134, and enters the nostrils and respiratory tract 140 (e.g., nasal passageways) of the user. In some embodiments, a device other than a nasal cannula 134 may be used to direct the acoustic jet of air 170 into the nasal passageways of the user.

As stated above, the oscillatory motion of the vibrating element 120 creates an acoustic jet of air 170 that exits the orifice 115 of the actuator housing 110. The flow of an acoustic jet has the characteristic of coherence. Conventional jets or air or other fluid, such as those used by existing ventilators and CPAP devices, produce a laminar flow of air that transitions into turbulent flow of air, which disperses very quickly as a free jet. However, the acoustic jets of air generated by embodiments of the present disclosure are defined by a train of vortices 172 that remain coherent in shape (i.e., the acoustic jet of air has a lower rate of dispersion) and produce high rates of the flow. The acoustic pressure inducer 100 generates a pair of vortices 172 at each cycle during the ejection phase (when air is pushed out of the cavity). More particularly, the acoustic jets of air are formed from the time harmonic motion of the vibrating element 120 that encloses the acoustic chamber 116 along with the orifice 115. During each cycle, the vibrating element 120 moves toward the orifice 115 and a slug of fluid is removed from the cavity out of the orifice 115. A vortex sheet is formed at the edge of the orifice, which roles into a vortex pair 172. The vortex pair 172 then advects downstream under its own induced velocity as a pulse of air 173. The vortex pair 172 is removed enough from the orifice 115 of the actuator housing 110 that the entrained air into the cavity during the suction phase does not affect the vortex pair 172 exiting the orifice 115. Based on the operating frequency of the vibrating element 120, this process can be repeated tens/hundreds/thousands of times in each second. Patients may not be able to discern that the air flow is actually composed from a train of vortices 172 and/or pulses of air 173, and may experience the acoustic jet of air 170 as if it were a continuous jet.

The enhanced celerity of acoustic jet of air 170 is associated with the ability of the flow to sustain high momentum (i.e., penetration of the flow) for longer distances. The vortex pairs 174 that exit the nasal cannula 134 will enter the nostril and respiratory tract 140 without significant reflection and/or loss to the environment. The acoustic pressure inducer 100 generates pressure (i.e., "power") that is sufficient to keep the passageways of the respiratory tract from collapsing and causing occlusion.

In addition to higher penetration of flow, another advantage of the embodiments described herein is the ability to direct air pressures specifically to the occluded area of the respiratory tract 140. Use of an acoustic jet of air 170 enables airstreams to be produced that will selectively flow to areas of greater resistance based on the principle of impedance matching. The coherent structure of the jet, together with the ability to match the impedance of the acoustic jet of air 170 with the impedance of the airway (e.g., nasal passageways/respiratory tract 140), eliminates the need for a closed system that requires a mask. The impedance of the acoustic jet of air 170 may be matched to the impedance of the patient's airway (i.e., nasal passageways/respiratory tract 140).

According to the concept of impedance matching, the maximum power transfer (i.e., with minimum reflections) occurs when the impedance of the source (input) matches the impedance of the load (output). In a branch network, the power transfer will be maximized to the branch that carries the closest impedance of the source. Matching of the acoustic impedance of the acoustic jet of air 170 to the impedance of the respiratory tract 140 enables one to direct the air flow to areas of higher resistance without global pressurization. It may ensure the most power (i.e., pressure) is transferred with the acoustic jet of air 170 and does not get lost (i.e., reflexed back to the open environment).

As described above, the acoustic jet of air 170 is formed by the time harmonic motion of the vibrating element 120. Therefore, the acoustic jet of air 170 is frequency dependent. The frequency of the acoustic jet depends on the resonant frequency of the acoustic chamber 116 and the and the mechanical resonance frequency of the vibrating element 120. By varying the geometry of the acoustic chamber 116, and/or the geometry of the orifice 115, and/or the type of the vibrating element 120, a very wide range of excitation frequencies can be used. There are other methods of adjusting the frequency. As an example and not a limitation, the force applied to the actuator housing 110 by the fasteners 117 (see FIGS. 2-8) that maintain the vibrating element 120 may also be varied to adjust the frequency. The impedance of the flow is directly related to frequency and, thus, the acoustic pressure inducer 100 described herein may produce acoustic jets of air 170 with varying impedance. In a branching tube, the majority of pulsatile flow in the upstream tube will go to the downstream branch with the closest impedance, even if this branch has a higher resistance than other branches in the system. Accordingly, embodiments described herein may deliver a flow of air to any area of interest, including areas of greater resistance.

Generally, different obstructive sleep apnea patients require different levels of air pressure to open their airways of the respiratory tract. This variation in the required air pressure necessary to open patients' airways may be caused by variation in the locations and severity of patients' airway blockage and/or degree of occlusion.

Embodiments of the present disclosure may produce a range of volumetric flow rates necessary to match its application by adjusting the coupling arrangement between the tube 130 and the orifice 115. Still referring to FIG. 1, in some embodiments, the first end 131 of the tube 130 may be offset with respect to the orifice 115 such that there is a gap g present between the tube 130 and the orifice 115. The vortex pair 172 that enters the tube 130 may create a strong localized negative pressure that in return causes entrainment flow to enter the tube 130 as well. The tube 130 uses entrained air to increase the overall flow rate that is produced by the acoustic pressure inducer 100. The overall flow rate may therefore be adjusted accordingly to match the specific pressure requirements for patient specific applications.

Figure 2:
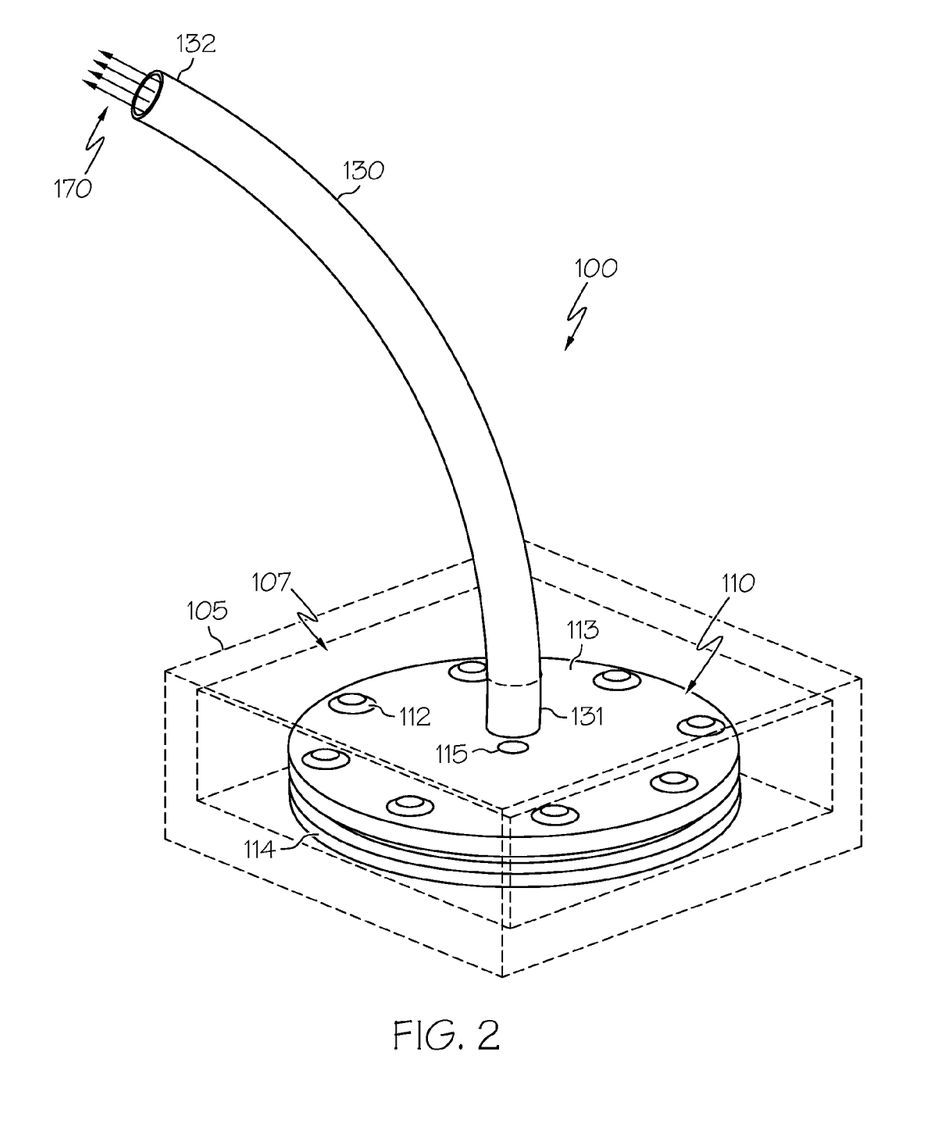
FIG. 2 depicts a isometric view of an exemplary acoustic pressure inducer according to one or more embodiments described and illustrated herein.
Figure 3:
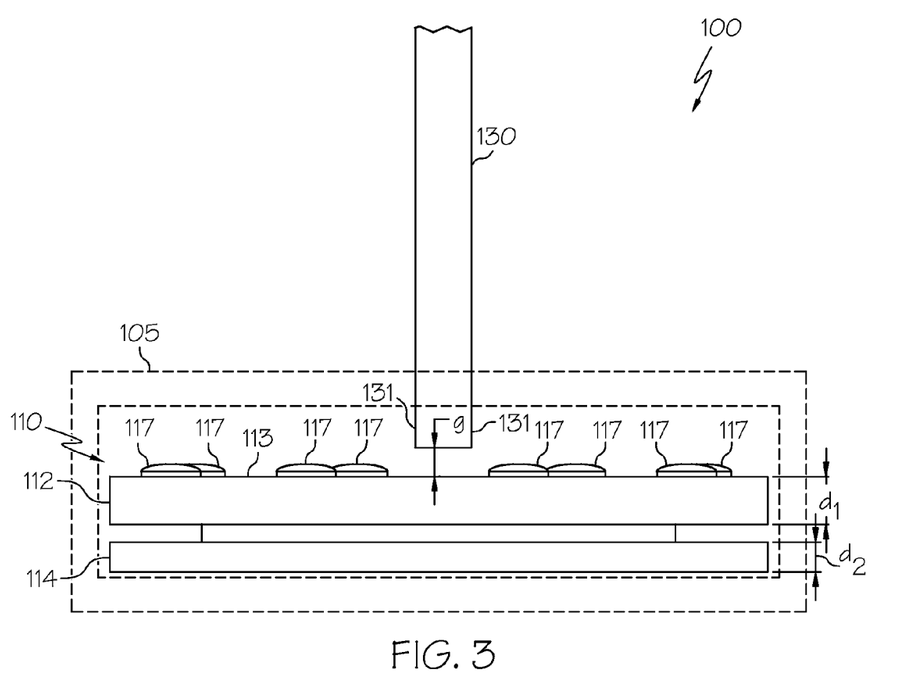
FIG. 3 depicts a side view of the exemplary acoustic pressure inducer depicted in FIG. 2 according to one or more embodiments described and illustrated herein.
Figure 4:
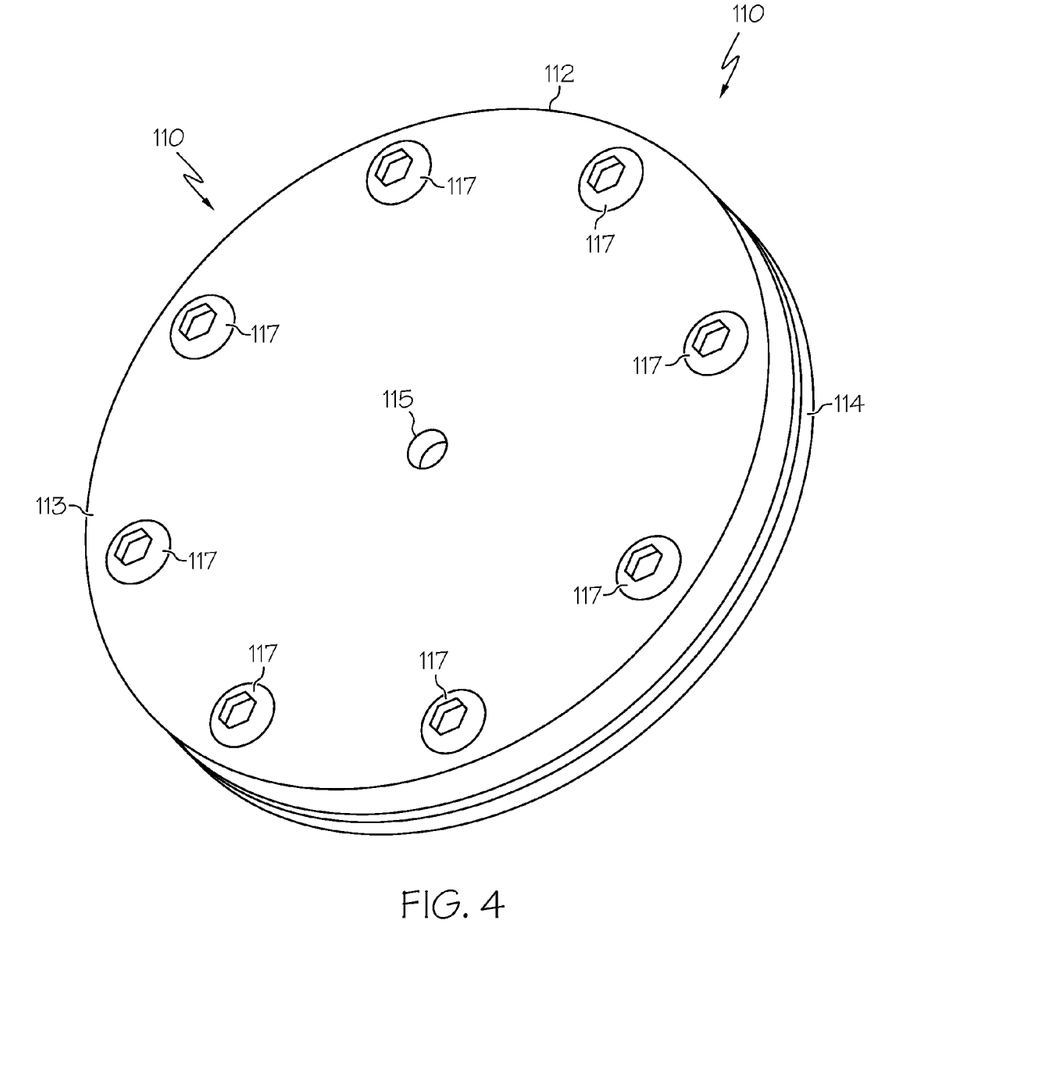
FIG. 4 depicts an isometric view of an actuator of the acoustic pressure inducer depicted in FIG. 2 according to one or more embodiments described and illustrated herein.
Figure 5:
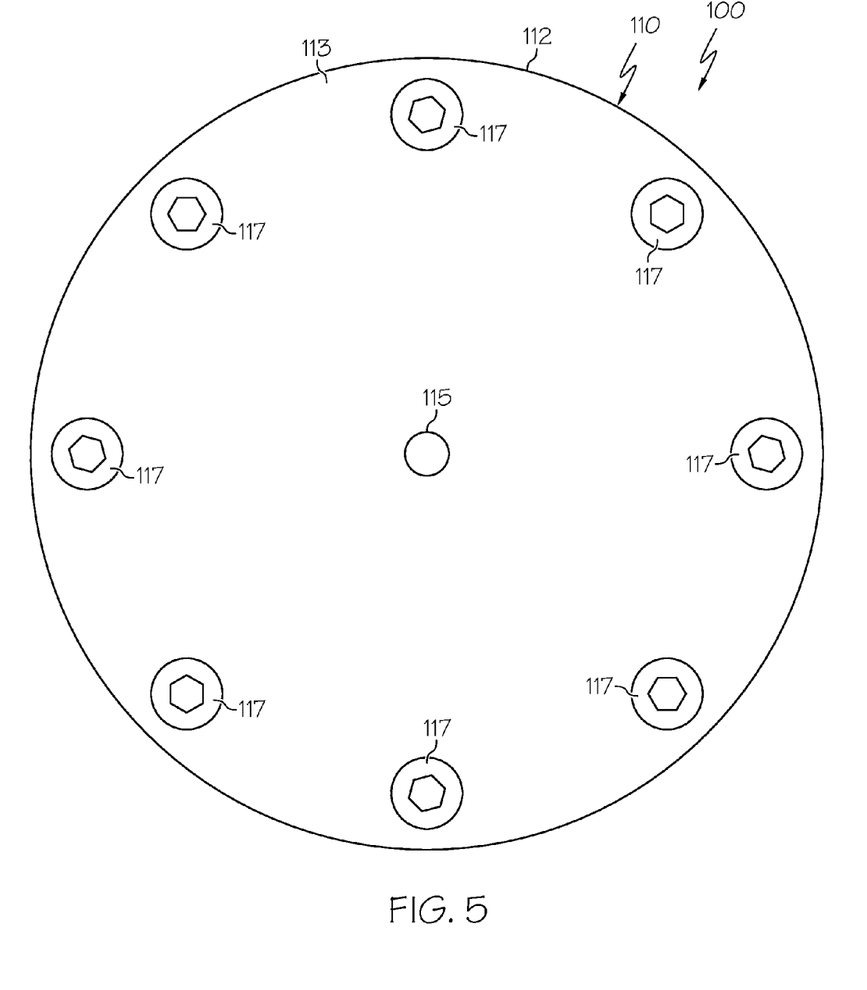
FIG. 5 depicts a top view of the actuator depicted in FIG. 4 according to one or more embodiments described and illustrated herein.
Figure 6:
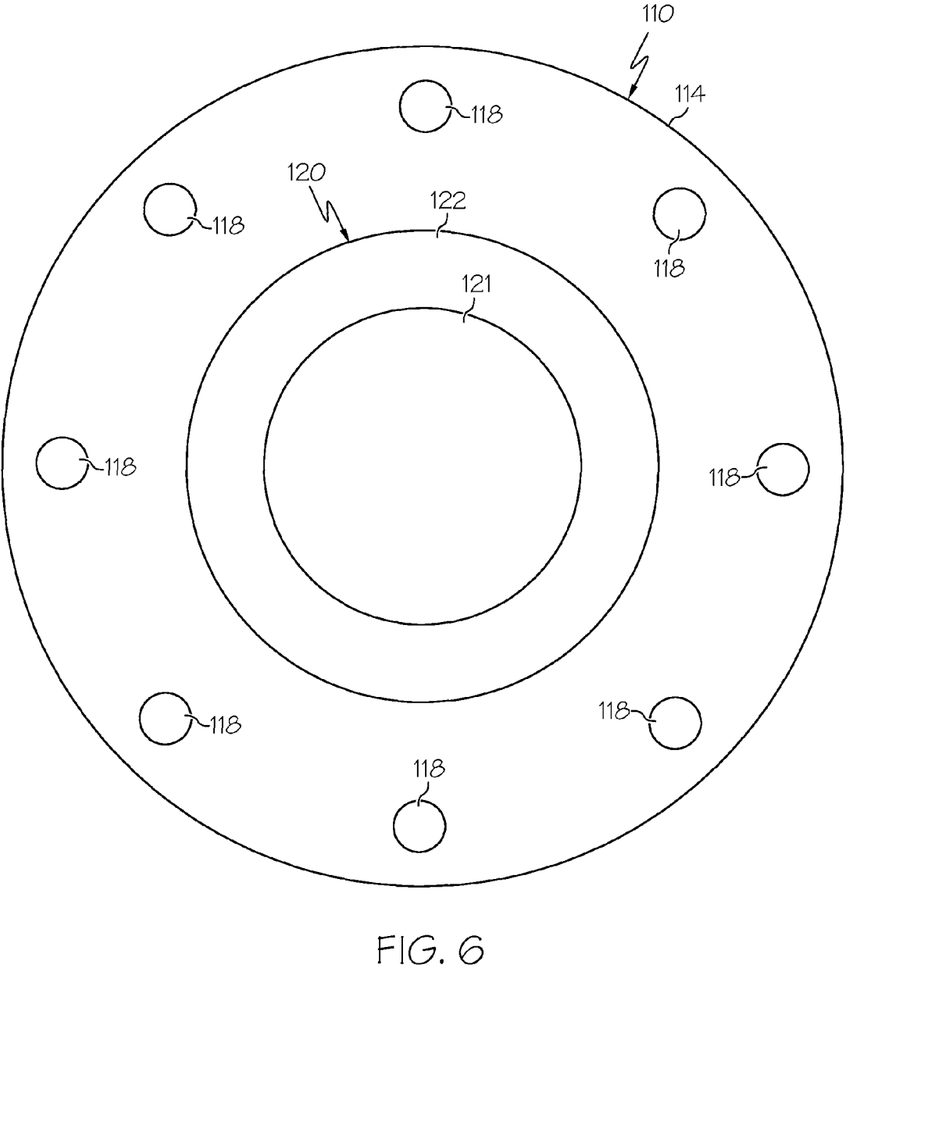
FIG. 6 depicts a bottom view of the actuator depicted in FIG. 4 according to one or more embodiments described and illustrated herein.
Figure 7:
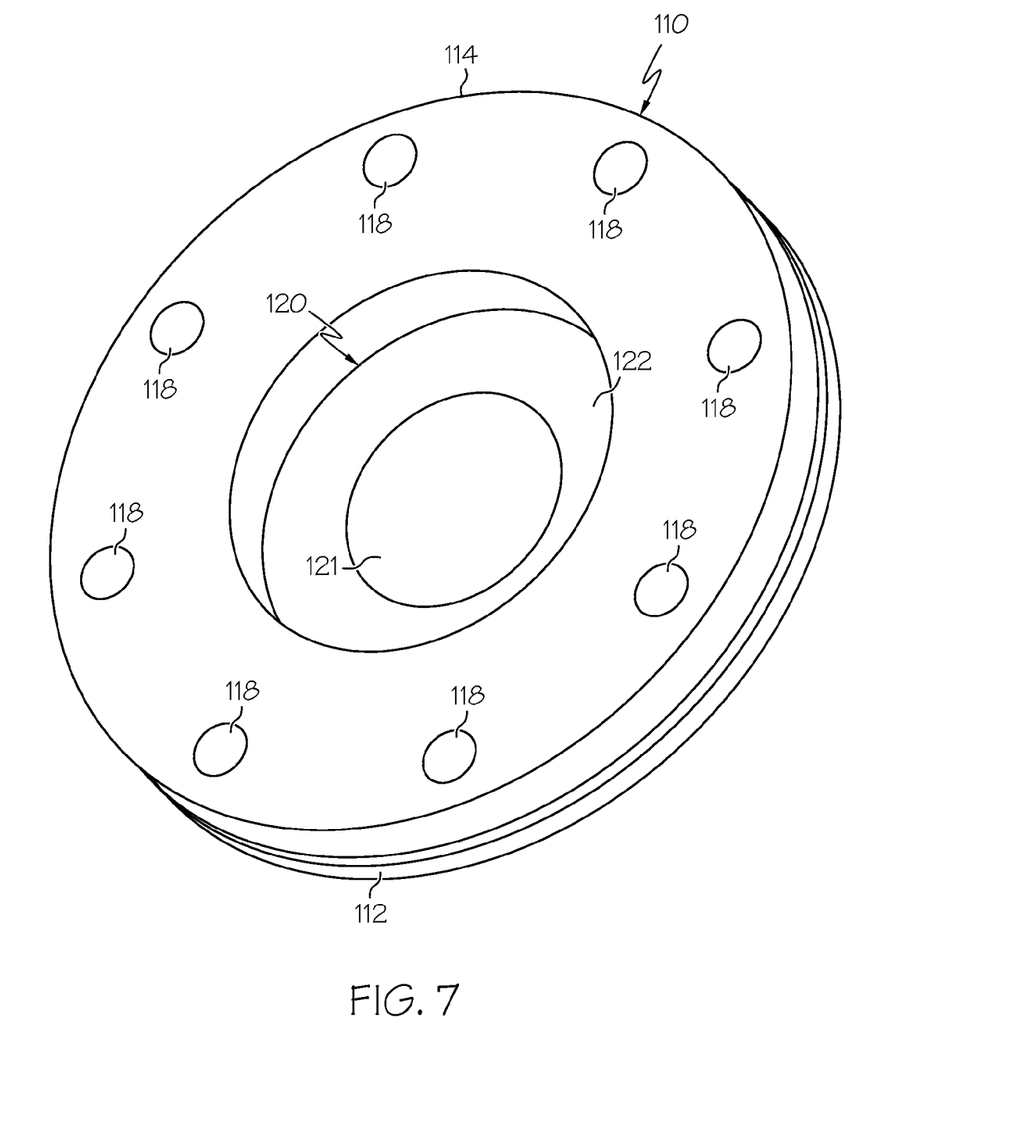
FIG. 7 depicts a bottom perspective view of the actuator depicted in FIG. 4 according to one or more embodiments described and illustrated herein.
Figure 8:
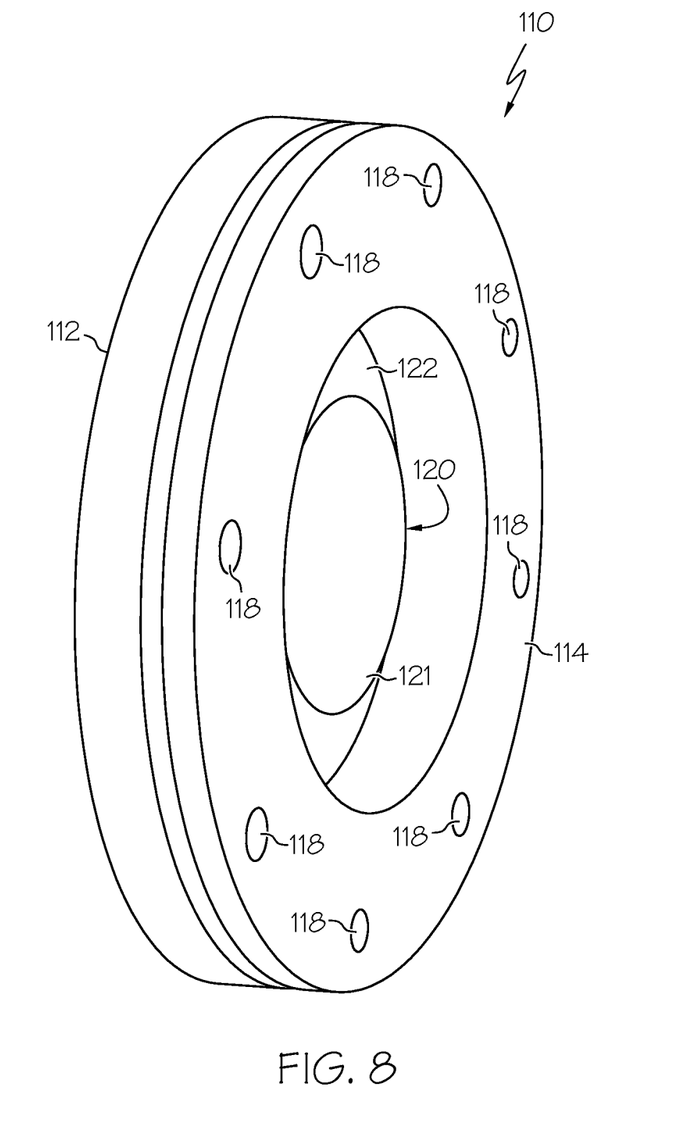
FIG. 8 depicts a side perspective view of the actuator depicted in FIG. 4 according to one or more embodiments described and illustrated herein.

Referring now to FIGS. 2-8, an exemplary acoustic pressure inducer 100 according to the schematic illustration of FIG. 1 is graphically illustrated in various views. FIG. 2 is an isometric, partially transparent view, and FIG. 3 is a side, partially transparent view, of the exemplary acoustic pressure inducer 100. FIG. 4 is an isometric view of an actuator 102 of the acoustic pressure inducer 100. FIG. 5 is a top view of the actuator 102, while FIG. 6 is a bottom view of the actuator 102, including the vibrating element 120. FIGS. 7 and 8 are perspective views of the actuator 102.

Referring to FIGS. 2 and 3, the illustrated acoustic pressure inducer 100 includes the actuator housing 110, vibrating element 120 (not visible in FIGS. 2 and 3), tube 130 and nasal cannula (not visible in FIGS. 2-8). In the illustrated embodiment, the actuator housing 110 is enclosed by an outer housing 105. For example, the actuator housing 110 may be secured within the enclosure 107 defined by the outer housing 105. Although not shown in FIGS. 2 and 3, the signal generator component 150 and power supply 160 may also be disposed in the enclosure 107 defined by outer housing 105. The tube 130 passes through the outer housing 105 and is fluidly coupled to a nasal cannula 134 for positioning in the nostrils of a patient. The outer housing 105 may provide acoustic insulation to eliminate operational noises that may otherwise disturb the user.

Now referring generally to FIGS. 2-8, the actuator housing 110 of the exemplary acoustic pressure inducer 100 includes a first housing half 112 and a second housing half 114. Although the first and second housing halves 112, 114 are illustrated as circular, embodiments are not limited thereto. The first and second housing halves 112, 114 may be fabricated from any suitably rigid material, such as aluminum, for example. As shown in FIGS. 7 and 8, the vibrating element 120 is supported by the first and second housing halves 112, 114. The vibrating element 120 of the illustrated embodiment is configured as a piezoelectric membrane 121 that is supported by a support member 122, as depicted in FIGS. 7-8. The support member 122 may be configured as a plate made of a suitably rigid material. The support member 122 is disposed between the first and second housing halves 112, 144. It should be understood that in embodiments that utilize a vibrating element of a configuration other than a piezoelectric member, the vibrating element 120 may be coupled to the actuator housing 110 in a different configuration. Further, the actuator housing 110 of such other embodiments may not include first and second circular housing halves 112, 114.

In the illustrated embodiment, the first housing half 112 is secured to the second housing half 114 via fasteners 117 positioned through holes 118 in each half. It should be understood that other coupling methods may be used, such as bonding, adhesive, clamps, and the like.

The first housing half 112 may have a thickness $d_1$ that is greater than a thickness $d_2$ of the second housing half 114. The thickness $d_1$ of the first housing half 112 may define a volume of the internal acoustic chamber 116 (see FIG. 1) between the upper surface of the first housing half 112 and the vibrating element 120. The upper surface 113 of the first housing half 112 includes an orifice 115 configured as an opening. Although the orifice 115 is illustrated as a circular opening in the first housing half 112, embodiments are not limited thereto. For example, the orifice 115 may also be configured as a slot opening, a cross opening, or other shaped openings. As shown in FIG. 3, the tube 130 may be offset from the orifice 115 by a gap g. The outer housing 105 may support the tube 130 at an offset orientation with respect to the orifice 115. The tube 130 may be made of any suitably pliable material, such as plastic, for example.

An acoustic pressure inducer 100 was built according to FIGS. 2-8 for evaluation purposes. Additionally, referring to FIG. 9, a 2:1 nasal model 200 replica of the airway passage 204 from the nostrils to the epiglottis 202 was constructed from CT scans taken along the upper nasal airway. Input flow to the model from the nostrils 206 simulated respiration performed by the acoustic pressure inducer 100. A single tube 130 was placed at a standoff distance from the orifice 115 at a first end 131 (see FIG. 2), and a second end 132 was placed about 3 mm away from the septum of the nostrils 206 of the nasal model 200.

Figure 9:
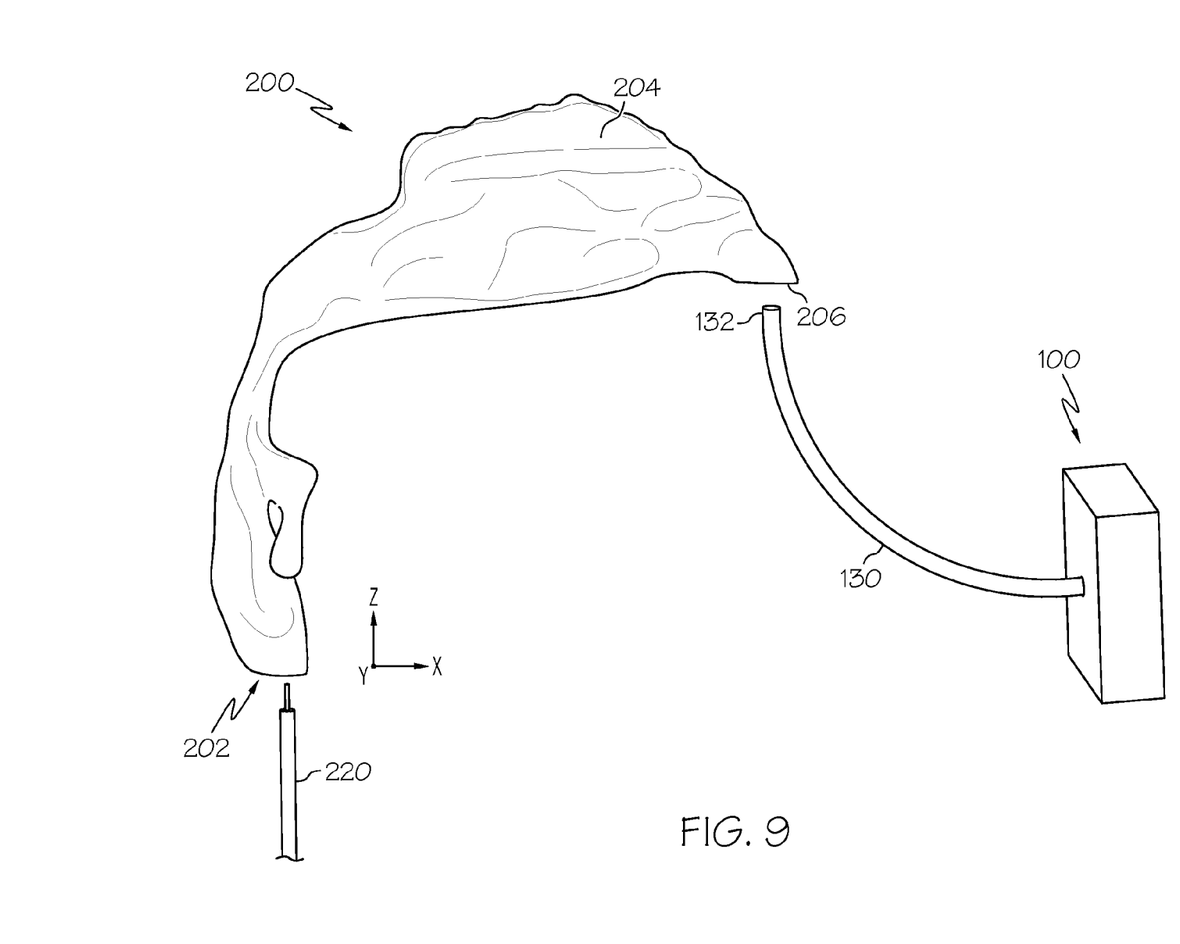
FIG. 9 schematically depicts a nasal model replica and an acoustic pressure inducer experiment arrangement.

The acoustic pressure inducer 100 was placed about half a foot away from the nasal model 200. Flow rate measurements were taken at the orifice 115 of the acoustic pressure inducer 100, at the exit of the tube 130, and at the exit of the nasal model 200 (e.g., output flow at the level of the epiglottis 202). For comparison, the same input parameters were used to measure the response of a conventional jet (e.g., same tube, same tube location with respect to the nostril 206, and same flow rate).

Figure 10:
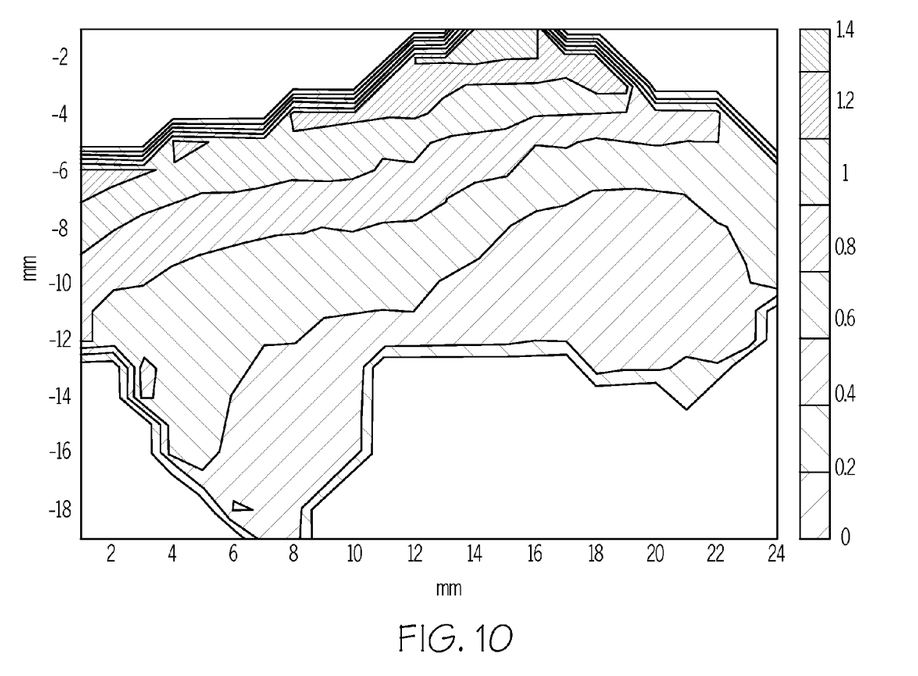
FIG. 10 is a graph depicting the flow distribution of airflow at an exit of a nasal passageway model according to one or more embodiments described and illustrated herein.

Measurement of airflow at the exit of the epiglottis 202 was complicated by its irregular shape. To accurately determine airflow at the level of the epiglottis, velocities were measured by using a computer controlled transverse to move the hot-wire probe at 1 mm increments along the x- and y-axes to cover the entire opening at the epiglottis 202. Velocity measurements were obtained at each increment, and the velocity distribution was intergraded to obtain the volume of the flow that was recovered. FIG. 10 shows a contour of the velocity distribution (m/s) at the epiglottis level of the flow produced by the acoustic jet.

The results are summarized in Table 1 below:

TABLE 1

Results for using an acoustic pressure inducer as ventilation method in standard liters per minute (slpm).

|  | Acoustic pressure inducer (slpm) | Conventional pressurized flow (slpm) |
|---|---|---|
| Actuator Flow Rate | 8.5 | n/a |
| Input flow rate at the nostrils | 17.5 | 17.5 |
| Output flow rate the level of the epiglottis | 14 | 2.7 |
| Percent Recovered | 80% | 15% |

Table 1 demonstrates that the acoustic pressure inducer may be an effective treatment for obstructive sleep apnea without the need for the tight seal required of traditional CPAP devices. That 80% of air flow is recovered at the exit of the epiglottis in this test model demonstrates the ability of the acoustic pressure inducer 100 to deliver airflow to areas of higher resistance without the need for a seal (enabled by impedance matching and higher flow penetration), and also indicates that the acoustically generated airflow throughout the entire upper nasal pharyngeal airway is likely sufficient to pressurize all clinically relevant anatomical areas where soft tissue collapse (obstructive sleep apnea) occurs. The poor recovery (15%) demonstrated with the conventional jet was expected as a tight seal was not used in the experiment, and exposes the current weakness of CPAP devices currently available to obstructive sleep apnea patients.

More particularly, without a seal, most of the conventional jet gets reflected and deflected from the nostril opening because of the pathways higher resistance. Flow would naturally take the path of least resistance; hence the higher resistance in the airway bars most the flow produced by conventional jet from entering into the nostril. Because of the momentum in the jet part of the airflow would get deflected (i.e., stir) to the sides and proceed around the nostril, and part of the flow would reflect back (i.e., reverse its direction). A small amount of air would actually enter the nostril. The acoustic jet of air has higher concentrated momentum because of its coherent properties, so it is able to penetrate more into the nostril pathway. If the impedance of the flow is match with the impedance of the airway, then all or most of the air flow produced by the acoustic jet should be able to proceed into the nostril.

Figure 11:
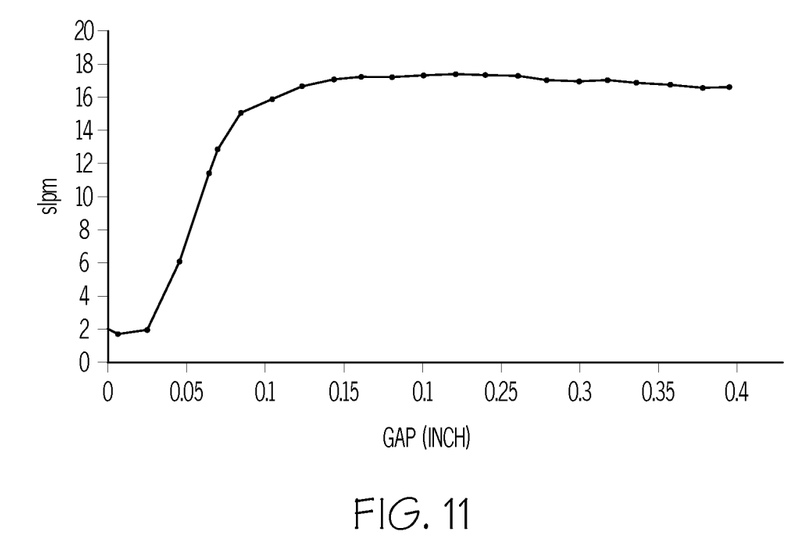
FIG. 11 is a graph depicting a flow rate of an exemplary acoustic pressure inducer as a function of a gap between an orifice and a tube according to one or more embodiments described and illustrated herein.

As described above, the gap g between the orifice 115 of the acoustic pressure inducer 100 and the tube 130 helps increase the overall flow rate that is produced by the acoustic pressure inducer 100. The volumetric flow rate that exits the tube 130 will depend on the driving amplitude and the frequency of the acoustic pressure inducer 100, on the height of the gap g, on the length of the tube 130, and on the inner diameter of the tube 130. FIG. 11 depicts how the measured flow rate from a 6 inch long tube with 0.43 inch inner diameter can vary by changing the height of the gap g between the tube 130 and the acoustic pressure inducer 100. It is shown that when the tube is connected directly to the orifice of the acoustic pressure inducer 100, or it is very close to it, there is a significant reduction in flow rate that is produced.

Figure 12:
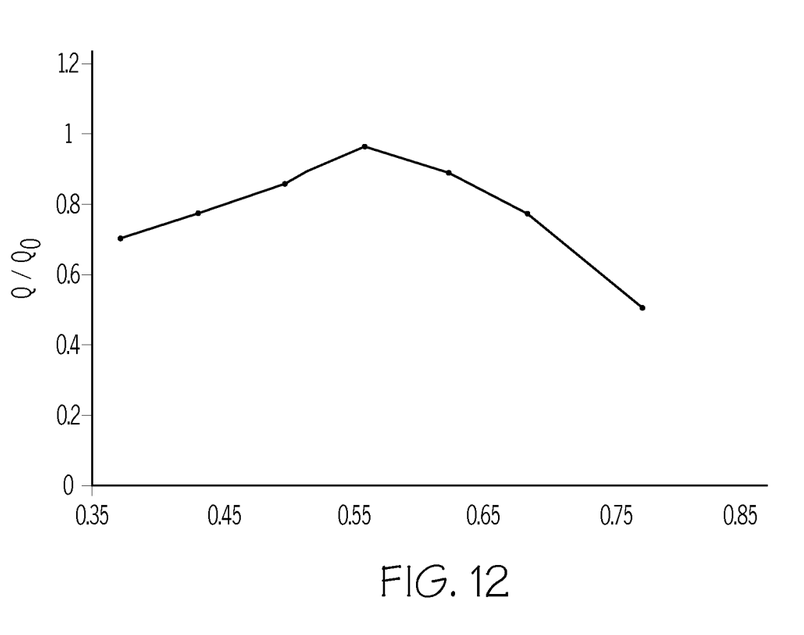
FIG. 12 is a graph depicting a flow rate of an exemplary acoustic pressure inducer as a function of a tube inside diameter according to one or more embodiments described and illustrated herein.
Figure 13:
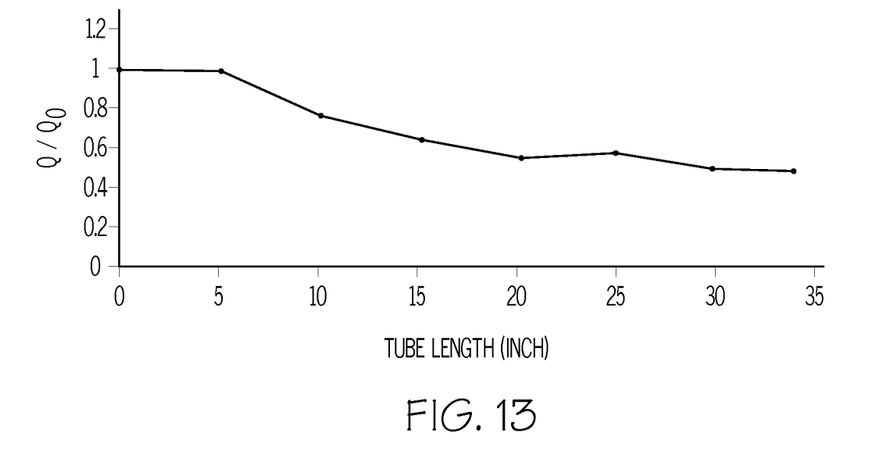
FIG. 13 is a graph depicting a flow rate of an exemplary acoustic pressure inducer as a function of tube length according to one or more embodiments described and illustrated herein.

FIG. 12 is a graph depicting how the volumetric flow rate can vary based on the inner diameter of the tube 130. The data was taken for 6 inch long tubes and using 0.25 inch gap g between the tube 130 and the orifice 115 of the acoustic pressure inducer 100. The graph shows that varying the inner diameter of the tube 130 can serve as another parameter that may be varied to adjust for the desired flow rate from the acoustic pressure inducer 100. FIG. 13 is a graph depicting how the flow rate changes with the length of the tube 130 (using 0.25 inch gap g between the tube 130 and the acoustic pressure inducer 100, and 0.5 inch flexible tube 130). The graph of FIG. 13 shows that the acoustic pressure inducer 100 can be placed at a reasonable distance away from the patient and still maintain a minimal decay of the volumetric flow rate.

It should now be understood that embodiments are directed to acoustic pressure inducers and methods for treatment of obstructive sleep apnea using coherent, acoustic flows of air. The acoustic jets of air are air streams that flow in a manner that disregards the observation that a pressurized gas or airstream will take the path of least resistance due to impedance matching between the acoustic jet and the respiratory tract. The acoustic pressure inducers described herein do not require a tight fitting mask or a nasal interface to provide a tight air seal at the patients' nostrils and mouth, and allow patients to open their mouths during sleep. Minimal tubing and equipment allow for increased freedom in sleep positions and may reduce the feeling of claustrophobia of patients. Further, the selective pressurization of the respiratory tract may reduce abdominal bloating.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. An acoustic pressure inducer for treatment of obstructive sleep apnea comprising:
    an actuator housing comprising an orifice;
    a tube having a first end and a second end, the first end fluidly coupled to the orifice of the actuator housing, wherein a gap is present between the first end of the tube and the orifice;
    a nasal cannula fluidly coupled to the second end of the tube, wherein the nasal cannula is configured to be positioned proximate to nostrils of a user;
    a vibrating element within the actuator housing, wherein the vibrating element and the actuator housing define an acoustic chamber that is fluidly coupled to the orifice; and
    a signal generator component electrically coupled to the vibrating element and configured to provide an electronic signal to the vibrating element to cause the vibrating element to oscillate within the actuator housing, wherein:
        oscillation of the vibrating element produces an acoustic jet of air comprising a train of vortices; and
        the acoustic jet of air exits the orifice and enters a nasal passageway of the user through the nasal cannula to prevent respiratory tract occlusion.

2. The acoustic pressure inducer of claim 1, wherein the vibrating element comprises a piezoelectric diaphragm.

3. The acoustic pressure inducer of claim 1, wherein the orifice comprises a slot in the actuator housing.

4. The acoustic pressure inducer of claim 1, wherein the actuator housing comprises multiple orifices.

5. The acoustic pressure inducer of claim 1, wherein a height of the gap is adjustable to vary a flow rate of the acoustic jet of air.

6. The acoustic pressure inducer of claim 1, wherein a frequency of the oscillation of the vibrating element is substantially equal to a resonant frequency of the vibrating element.

7. The acoustic pressure inducer of claim 1, further comprising an outer housing, wherein the actuator housing, the vibrating element and the signal generator component are disposed within the outer housing, and the tube extends from the outer housing.

8. The acoustic pressure inducer of claim 1, wherein the actuator housing further comprises:
    a first housing half, wherein the orifice is provided in the first housing half; and
    a second housing half, wherein the vibrating element is disposed between the first housing half and the second housing half.

9. The acoustic pressure inducer of claim 8, wherein the second housing half comprises a ring, and the vibrating element is disposed at an opening of the ring.

10. The acoustic pressure inducer of claim 1, wherein a frequency of the acoustic jet is such that an impedance of the acoustic jet of air is matched to an impedance of the nasal passageway.

11. The acoustic pressure inducer of claim 1, further comprising a battery power source electrically coupled to the signal generator component.

12. A method of treating obstructive sleep apnea, the method comprising:
    generating an acoustic jet of air comprising a train of vortices, wherein the acoustic jet of air is generated by oscillatory motion of a vibrating element within an actuator housing such that the acoustic jet of air exits an acoustic chamber defined by the vibrating element and the actuator housing through an orifice in the actuator housing; and directing the acoustic jet of air into a nasal passageway of a user through a nasal cannula.

13. The method of claim 12, wherein a seal is not present between the nasal cannula and nostrils of the user.

14. The method of claim 12, wherein the vibrating element comprises a piezoelectric diaphragm.

15. The method of claim 12, wherein the nasal cannula is fluidly coupled to a tube that is fluidly coupled to the orifice of the actuator housing.

16. The method of claim 15, wherein a gap is present between the tube and the orifice of the actuator housing.

17. The method of claim 16, further comprising adjusting a height of the gap to vary a flow rate of the acoustic jet of air.

18. The method of claim 12, further comprising adjusting the oscillatory motion of the vibrating element such that an impedance of the acoustic jet of air is matched to an impedance of the nasal passageway.

19. The method of claim 12, wherein a frequency of the oscillatory motion of the vibrating element is substantially equal to a resonant frequency of the vibrating element.

20. An acoustic pressure inducer for treatment of obstructive sleep apnea comprising:
an actuator housing comprising an orifice;
a tube having a first end and a second end, the first end fluidly coupled to the orifice of the actuator housing such that a gap is present between the first end of the tube and the orifice;
a vibrating element within the actuator housing, wherein the vibrating element and the actuator housing define an acoustic chamber that is fluidly coupled to the orifice; and
a signal generator component electrically coupled to the vibrating element and configured to provide an electronic signal to the vibrating element to cause the vibrating element to oscillate within the actuator housing, wherein:
oscillation of the vibrating element produces an acoustic jet of air comprising a train of vortices; and
the acoustic jet of air exits the orifice and enters a nasal passageway of a user through the second end of the tube without a fluid seal at nostrils of the user to prevent respiratory tract occlusion.

* * * * *